(12) United States Patent
Nakano et al.

(10) Patent No.: US 11,896,966 B2
(45) Date of Patent: Feb. 13, 2024

(54) ANTIBACTERIAL MATERIAL AND ANTIBACTERIAL FILM AND ANTIBACTERIAL MEMBER USING THE SAME

(71) Applicants: KABUSHIKI KAISHA TOSHIBA, Tokyo (JP); TOSHIBA MATERIALS CO., LTD., Kanagawa (JP)

(72) Inventors: Kayo Nakano, Yokohama (JP); Akira Sato, Yokohama (JP); Yasuhiro Shirakawa, Yokohama (JP); Keiichi Fuse, Yokohama (JP); Shinya Kasamatsu, Yokohama (JP); Akito Sasaki, Yokohama (JP)

(73) Assignees: KABUSHIKI KAISHA TOSHIBA, Tokyo (JP); TOSHIBA MATERIALS CO., LTD., Yokohama (JP)

( * ) Notice: Subject to any disclaimer, the term of this patent is extended or adjusted under 35 U.S.C. 154(b) by 944 days.

(21) Appl. No.: 16/872,554

(22) Filed: May 12, 2020

(65) Prior Publication Data

US 2020/0338543 A1 Oct. 29, 2020

Related U.S. Application Data

(63) Continuation of application No. 12/874,849, filed on Sep. 2, 2010, now abandoned, which is a continuation of application No. PCT/JP2009/000981, filed on Mar. 4, 2009.

(30) Foreign Application Priority Data

Mar. 4, 2008 (JP) .................. 2008-054141
Mar. 4, 2008 (JP) .................. 2008-054143
Dec. 19, 2008 (JP) .................. 2008-324275

(51) Int. Cl.
| | |
|---|---|
| A01N 59/16 | (2006.01) |
| C01G 41/02 | (2006.01) |
| A01N 59/20 | (2006.01) |
| A01P 1/00 | (2006.01) |
| B01J 35/00 | (2006.01) |
| B01J 23/68 | (2006.01) |
| B01J 23/30 | (2006.01) |
| B82Y 30/00 | (2011.01) |
| C01G 41/00 | (2006.01) |
| A61L 2/232 | (2006.01) |
| B01J 23/652 | (2006.01) |
| B01J 23/34 | (2006.01) |
| A61L 9/014 | (2006.01) |
| A61L 2/238 | (2006.01) |
| A61L 9/012 | (2006.01) |

(Continued)

(52) U.S. Cl.
CPC ............. *B01J 35/004* (2013.01); *A61L 2/232* (2013.01); *A61L 2/238* (2013.01); *A61L 9/012* (2013.01); *A61L 9/014* (2013.01); *B01J 23/30* (2013.01); *B01J 23/34* (2013.01); *B01J 23/6527* (2013.01); *B01J 23/687* (2013.01); *B01J 23/888* (2013.01); *B82Y 30/00* (2013.01); *C01G 41/00* (2013.01); *C01G 41/02* (2013.01); *C09D 5/14* (2013.01); *C09D 7/61* (2018.01); *C09D 7/67* (2018.01); *C09D 7/68* (2018.01); *A61L 2209/21* (2013.01); *B01J 35/023* (2013.01); *B01J 37/0036* (2013.01); *C01P 2002/52* (2013.01); *C01P 2002/72* (2013.01); *C01P 2004/62* (2013.01); *C01P 2004/64* (2013.01); *C01P 2006/12* (2013.01); *C08K 3/22* (2013.01)

(58) Field of Classification Search
CPC ...................................................... A61L 2/232
See application file for complete search history.

(56) References Cited

U.S. PATENT DOCUMENTS

| 8,173,573 B2 | 5/2012 | Nakano et al. |
| 2002/0005145 A1 | 1/2002 | Sherman |

(Continued)

FOREIGN PATENT DOCUMENTS

| EP | 1 801 815 A1 | 6/2007 |
| JP | 60-181002 A | 9/1985 |

(Continued)

OTHER PUBLICATIONS

M. Pham TH, et al., "Raman Study of WO3 Thin Films", Solid State Ionics, vol. 14, Dec. 31, 1984, pp. 217-220, XP002656915.

(Continued)

*Primary Examiner* — Sarah Alawadi
(74) *Attorney, Agent, or Firm* — Foley & Lardner LLP

(57) ABSTRACT

In one embodiment, an antibacterial material includes at least one microparticles selected from tungsten oxide microparticles and tungsten oxide complex microparticles. The microparticles, which have undergone a test to evaluate viable cell count by inoculating in a test piece, to which the microparticles are adhered in a range of 0.02 mg/cm² or more and 40 mg/cm² or less, at least one bacterium selected from among *Staphylococcus aureus, Escherichia coli, Klebsiella pneumoniae, Pseudomonas aeruginosa*, methicillin-resistant *Staphylococcus aureus*, and enterohemorrhagic *Escherichia coli*, and storing for 24 hours, have an antibacterial activity value R of 0.1 or more expressed by the following: $R=\log(B_1/C_1)$ where, $B_1$ denotes an average value (number) of viable cell count after storing an untreated test piece for 24 hours, and $C_1$ denotes an average value (number) of viable cell count after storing the test piece on which the microparticles are coated for 24 hours.

9 Claims, No Drawings

(51) Int. Cl.
  *B01J 23/888* (2006.01)
  *C09D 5/14* (2006.01)
  *C09D 7/61* (2018.01)
  *C09D 7/40* (2018.01)
  *B01J 35/02* (2006.01)
  *B01J 37/00* (2006.01)
  *C08K 3/22* (2006.01)

(56) References Cited

U.S. PATENT DOCUMENTS

| | | |
|---|---|---|
| 2004/0139888 A1 | 7/2004 | Yadav et al. |
| 2005/0025700 A1 | 2/2005 | Bulian |
| 2005/0274833 A1 | 12/2005 | Yadav et al. |
| 2006/0210810 A1 | 9/2006 | Harris |
| 2007/0177372 A1 | 8/2007 | Matsuda et al. |
| 2007/0187653 A1 | 8/2007 | Takeda et al. |
| 2008/0119352 A1 | 5/2008 | Kitaguchi |
| 2008/0308775 A1 | 12/2008 | Yabuki |
| 2009/0023583 A1 | 1/2009 | Nakano et al. |
| 2010/0113254 A1 | 5/2010 | Sato et al. |
| 2010/0204041 A1 | 8/2010 | Nakano et al. |

FOREIGN PATENT DOCUMENTS

| | | | |
|---|---|---|---|
| JP | 02-006339 A | | 1/1990 |
| JP | 07-102678 A | | 4/1995 |
| JP | 08-296031 A | | 11/1996 |
| JP | 2001-081409 A | | 3/2001 |
| JP | 2001-152130 A | | 6/2001 |
| JP | 2004051644 | * | 2/2004 |
| JP | 2004-090590 A | | 3/2004 |
| JP | 2004-195439 A | | 7/2004 |
| JP | 2004-300648 A | | 10/2004 |
| JP | 2006055697 | | 3/2006 |
| JP | 2006-131583 A | | 5/2006 |
| JP | 2008-006429 A | | 1/2008 |
| JP | 2009-202152 A | | 9/2009 |
| WO | WO-2007/088891 | | 8/2007 |
| WO | WO-2007/093808 A2 | | 8/2007 |
| WO | WO-2008/117655 A1 | | 10/2008 |
| WO | WO-2009/031316 A1 | | 3/2009 |

OTHER PUBLICATIONS

M. Ladouceur et al., "Plasma-Sprayed Semiconductor Electrodes: Photochemical Characterization and NH3 Photoproduction by Substoichiometric Tungsten Oxides", J. Phys. Chem, vol. 94, Dec. 31, 1990, pp. 4579-4587, XP002656977.

M. Penza et al., "NOx Gas Sensing Characteristics of W03 Thin Films Activated By Noble Metals (Pd, Pt, Au) Layers", Sensors and Actuators B, Dec. 31, 1998, pp. 52-59, XP002656978.

Hiroharu Kawasaki, "Properties of Metal Doped Tungsten Oxide Thin Films for Nox Gas Sensors Grown by PLD Method Combined With Sputtering Process", Sensors and Actuators B, vol. 100, Dec. 31, 2004, pp. 266-269, XP002656979.

Bhuiyan, M.H. et al., "Gas Sensing Properties of Metal Doped W03 Thin Film Sensors Prepared by Pulsed Laser Deposition and DC Sputtering Process", Japanese Journal of Applied Physics, vol. 45, Dec. 31, 2006, pp. 8469-8472, XP002656980.

Tetsu Tatsuma et al., "Bactericidal Effect of an Energy Storage Ti02—W03 Photocatal YST in Dark", Electrochemistry Communications, vol. 5, Dec. 31, 2003, pp. 793-796, XP002656981.

Yafeng Guo et al., "High Photocatalytic Capability of Self-Assembled Nanoporous W03 With Preferential Orientation Of (002) Planes", Environ. Sci. Technol., vol. 41, Dec. 31, 2007, pp. 4422-4427, XP002656982.

"Journal of Japan Sewage Works Association, Collection of papers" Jan. 2005; No. 507; vol. 42; pp. 163-174.

Y. Shimizu et al., "Reactive Evaporation of Metal Wire and Microdeposition of Metal Oxide Using Atmospheric Pressure Reactive Microplasma Jet", Japanese Journal of Applied Physics, 2006, vol. 45, No. 108 pp. 8228-8234.

M. Kurumada et al., "Structure of W03 ultrafine particles and their characteristic solid states", Journal of Crystal Growth, Feb. 15, 2005, vol. 275, Issues 1-2, pp. e1673-e1678.

JIS Z 2801, "Antimicrobial products—Test for antimicrobial activity and efficacy", Japanese Industrial Standard, and English Translation, May 20, 2006.

JIS R 1702, "Fine ceramics (advanced ceramics, advanced technical ceramics)—Test method for antibacterial activity of photocatalytic products under photoirradiation and efficacy", Japanese Industrial Standard, 2006.

JIS Z 9112, "Classification of fluorescent lamps by chromaticity and colour rendering property", Japanese Industrial Standard, 2004.

Translation of International Preliminary Report on Patentability of PCT/JP2009/000981, dated Oct. 21, 2010, 6 pages.

G.R. Bamwenda, et al.; The visible light induced photocatalytic activity of tungsten trioxide powders, Applied Catalysis A: General, VI. 210, No. 1-2; pp. 181-191, Feb. 23, 2001.

Tetsu Tatsuma, et al.; "Mechanism and Applications of Energy Storage Photocalyst", DOI: 10.1380/jssj. 24.13; vol. 24, No. 1; pp. 13-18; Jan. 10, 2003.

Japanese Office Action dated Mar. 1, 2016 issued in corresponding Japanese Application No. 2015-025563 and its English translation thereof.

Leake et al. Epitaxial Growth of WO3 Films on SrTiO3 and Sapphire. Appl. Phys. 33 (2000) 1048-1053. http://iopscience.iop.org/0022-3727/33/9/303/pdf/d00903.pdf.

Lu, Synthesis of Nano-Structured Monoclinic W03 Particles, Aug. 2001.

Solarska et al. Electrochromic and structural characteristics of mesoporous W03 films prepared by a sol-gel method. Jul. 2004.

Mohammad et al. Phase Transformations in W03 Thin Films Durng Annealing. Feb. 2002.

Rao Structure and Properties of Tungsten Tiroxide Thin Films for Electrochromic Device Application. Jan. 2013.

* cited by examiner

ANTIBACTERIAL MATERIAL AND ANTIBACTERIAL FILM AND ANTIBACTERIAL MEMBER USING THE SAME

CROSS-REFERENCE TO RELATED APPLICATION

This application is a continuation of U.S. application Ser. No. 12/874,849, filed on Sep. 2, 2010, which is a continuation of prior International Application No. PCT/JP2009/000981, filed on Mar. 4, 2009 which is based upon and claims the benefit of priority from Japanese Patent Application No. 2008-054141, filed on Mar. 4, 2008, No. 2008-054143, filed on Mar. 4, 2008, and No. 2008-324275, filed on Dec. 19, 2008; the entire contents of all of which are incorporated herein by reference.

FIELD

Embodiments described herein relate generally to an antibacterial material and an antibacterial film and antibacterial member using the same.

BACKGROUND

In recent years, antibacterial properties are demanded from a hygiene viewpoint for products such as straps and handrails touched by many and unspecified number of people, products such as stationery and kitchenware touched by hand, and all products such as interior materials, fibrous products and the like in dwelling environments, and therefore, antibacterial agents are being used. As the antibacterial agents, there are known organic and inorganic antibacterial agents. It is known that metal ions such as silver, copper and zinc have antibacterial properties, and there is used an inorganic antibacterial agent which has an antimicrobial metal component supported on mineral particles of zeolite or the like by ion exchange (see JP-A 60-181002 (KOKAI)). But, the antibacterial agent using antibacterial metal ions has disadvantages that it costs high, and has a possibility of causing metal allergy, a short period of retaining the performance, etc.

Antibacterial products which have a coating or coated film of titanium oxide as a photocatalyst formed on a base material surface or mixed into the material have been put into practical use (see JP-A 07-102678 (KOKAI) and JP-A 2001-081409 (KOKAI)). Since the photocatalyst composed of the titanium oxide is excited by ultraviolet light only, its performance is insufficient in an indoor environment where ultraviolet light is low. As countermeasures, there have been developed a visible light-responsive photocatalyst of titanium oxide having a platinum compound impregnated or titanium oxide having nitrogen or sulfur doped which exhibits its performance under visible light. But, the visible light-responsive photocatalyst based on titanium oxide has narrow excitation wavelength and does not provide enough performance under general indoor lighting. The antibacterial agent is demanded to decrease the number of bacteria to 1% or less. Currently, there has been obtained no antibacterial agent which is based on titanium oxide and exhibits the above performance.

Products required to have antibacterial properties have many applications used in places where light irradiation is low. For example, a living room of a general house has an illuminance of about 500 lx to 150 lx, and ceilings, walls, floors, furniture and places having home electric appliances expected to have antibacterial properties have a very low illuminance of about 50 lx. Especially, a washroom and a bathroom where antibacterial properties are required have an illuminance of less than 50 lx. Stationery and kitchen goods are kept on a shelf or in a drawer and not exposed to light. Since light irradiation enough to excite the photocatalyst cannot be obtained in a general indoor environment, the antibacterial agent using the photocatalyst cannot fully exhibit its performance. To improve the above point, antibacterial agents based on the photocatalyst added with metal ions such as silver, copper and zinc have been developed but sufficient performance has not been obtained.

Tungsten oxide has a bandgap smaller than that of titanium oxide and therefore attracts attention as a material capable of providing a photocatalytic action by visible light. The antibacterial action of tungsten oxide is described in, for example, "Journal of Japan Sewage Works Association, Collection of papers" 2005, No. 507, Vol. 42 that the growth of sulfur-oxidizing bacteria in an atmosphere of pH 2.5 is retarded. In addition, it is also known that antibacterial properties by the photocatalytic action can be obtained by mixing with titanium oxide. But, the antibacterial agent based on the conventional tungsten oxide requires special conditions such as an acidic condition, irradiation of near-ultraviolet rays, etc., and its application products are limited.

As described above, the conventional antibacterial agent has problems that it requires the irradiation of special light, sustainability of performance is insufficient, and the like. Especially, ultraviolet light required for excitation of an antibacterial agent based on titanium oxide is poor and its illuminance is also low in the interior of a general house, so that the irradiation of light sufficient for the product to exert the antibacterial performance cannot be obtained. In addition, light is not irradiated to stationery and kitchen goods kept on a shelf or in a drawer. Products used in a general dwelling environment are expected to exhibit antibacterial properties in a place where an illuminance of light is low and also in a dark place.

DETAILED DESCRIPTION

According to one embodiment, there is provided an antibacterial material including at least one microparticles selected from tungsten oxide microparticles and tungsten oxide complex microparticles. The microparticles, which have undergone an antibacterial property evaluation test to evaluate viable cell count by inoculating in a test piece, to which the microparticles are adhered in a range of 0.02 mg/cm$^2$ or more and 40 mg/cm$^2$ or less, at least one bacterium selected from among *Staphylococcus aureus, Escherichia coli, Klebsiella pneumoniae, Pseudomonas aeruginosa,* methicillin-resistant *Staphylococcus aureus,* and enterohemorrhagic *Escherichia coli,* and storing for 24 hours by a method according to Antimicrobial products—Test for antimicrobial activity of JIS-Z-2801 (2000), have an antibacterial activity value R of 0.1 or more expressed by the following:

$$R = \log(B_1/C_1)$$

where, $B_1$ denotes an average value (number) of viable cell count after storing an untreated test piece for 24 hours, and $C_1$ denotes an average value (number) of viable cell count after storing the test piece on which the microparticles are coated for 24 hours.

According to one embodiment, there is provided an antibacterial film including the antibacterial material of the embodiment, and an antibacterial member including the antibacterial material of the embodiment or the antibacterial film of the embodiment.

The antibacterial material according to the embodiment includes at least one microparticles (hereinafter referred to as tungsten oxide type microparticles) selected from tungsten oxide microparticles and tungsten oxide complex microparticles. The tungsten oxide type microparticles have a property that an antibacterial activity value R is 0.1 or more when an antibacterial property evaluation test is performed with the microparticles adhered in a range of 0.02 to 40 mg/cm$^2$ to a test piece. In addition, the tungsten oxide type microparticles preferably have a property that an antibacterial activity value $R_D$ is 0.1 or more when the antibacterial property evaluation test is performed in a dark place.

It is determined that the test for evaluating antibacterial performance (antibacterial property evaluation test) is performed by a method according to Antimicrobial products—Test for antimicrobial activity of JIS-Z-2801 (2000). The antibacterial activity value R is determined by inoculating at least one bacterium, which is selected from among *Staphylococcus aureus, Escherichia coli, Klebsiella pneumoniae, Pseudomonas aeruginosa*, methicillin-resistant *Staphylococcus aureus*, and enterohemorrhagic *Escherichia coli*, in a test piece to which tungsten oxide type microparticles to be evaluated are adhered in a range of 0.02 to 40 mg/cm$^2$, measuring an average value (number) $C_1$ of viable cell count after storing for 24 hours and an average value (number) $B_1$ of viable cell count of an untreated test piece in which the same bacterium is inoculated and stored for 24 hours, and calculating based on the following equation (1) according to the average values $C_1$ and $B_1$ of the viable cell counts.

$$R = \log(B_1/C_1) \quad (1)$$

The antibacterial activity value $R_D$ is determined by evaluating in the same manner as the antibacterial activity value R except that the evaluation sample is stored in a dark place. The antibacterial activity value $R_D$ is determined by inoculating at least one bacterium, which is selected from among *Staphylococcus aureus, Bacillus coli*, pneumobacillus, *Pseudomonas aeruginosa*, methicillin resistant *Staphylococcus aureus*, and enterohemorrhagic *Escherichia coli*, in a test piece to which tungsten oxide type microparticles are adhered in a range of 0.02 to 40 mg/cm$^2$, measuring an average value (number) $C_D$ of viable cell count after storing in the dark for 24 hours and an average value (number) $B_D$ of viable cell count of an untreated test piece in which the same bacterium is inoculated and stored in the dark for 24 hours, and calculating based on the following equation (2) according to the average values $C_D$ and $B_D$ of the viable cell counts.

$$R_D = \log(B_D/C_D) \quad (2)$$

To evaluate the antibacterial properties of the tungsten oxide type microparticles, microparticles (fine powder) are mixed with a dispersion medium such as water, and a dispersion process is performed by an ultrasonic disperser, a wet jet mill, a bead mill and the like to produce a dispersion liquid. A sample is produced by coating the obtained dispersion liquid on a test piece such as a glass plate by a general method such as dripping, spin coating, dipping, spraying or the like. The sample is evaluated for antibacterial properties by inoculating bacteria. When the tungsten oxide type microparticles have photocatalytic performance, it is preferable to determine a condition so that powder is not strained excessively by the dispersion process, thereby exerting photocatalytic performance in a state coated on the surface of the test piece.

The antibacterial material having the tungsten oxide type microparticles is not limited to the tungsten oxide type microparticles only but includes materials produced by known methods, such as a material having the microparticles coated on a base material, a material having the microparticles kneaded into a base material or textiles, a material having a surface layer containing the microparticles formed by a base material forming step, etc. To evaluate the above materials for antibacterial performance, test pieces are cut out from the above materials to perform the evaluation test. As a method of coating the microparticles on the base material, there is a method of using a dispersion liquid which is produced by performing the dispersion process on a mixture of powder, a dispersion medium and a dispersant if necessary similar to the antibacterial property evaluation test of the microparticles. If the film is required to have uniformity, it is preferable that a method such as spin coating, dipping, spraying or the like is applied as a coating method.

Since at least microparticles selected from tungsten oxide microparticles and tungsten oxide complex microparticles used in this embodiment have very high dispensability, a film which exerts antibacterial performance can be formed. Since conventional tungsten oxide particles having a large grain diameter cannot form a film on the base material, the antibacterial properties cannot be evaluated. In addition, a film exhibiting the antibacterial performance cannot be obtained by using tungsten oxide particles having a large grain diameter.

The tungsten oxide type microparticles used for the antibacterial material of this embodiment have properties that an antibacterial activity value R is 0.1 or more and also an antibacterial activity value $R_D$ is 0.1 or more. In other words, the tungsten oxide type microparticles exhibit excellent antibacterial performance to at least one bacterium selected from among *Staphylococcus aureus, Escherichia coli, Klebsiella pneumoniae, Pseudomonas aeruginosa*, methicillin-resistant *Staphylococcus aureus*, and enterohemorrhagic *Escherichia coli* when the amount of the microparticles adhered to the test piece is determined to be in a range of 0.02 to 40 mg/cm$^2$. The antibacterial performance of the tungsten oxide type microparticles is exerted without irradiation of special light and also exerted in a dark place.

Thus, the tungsten oxide type microparticles used for the antibacterial material exerts the antibacterial performance without requiring irradiation of special light. Therefore, practical antibacterial performance can be obtained even when the antibacterial material including the tungsten oxide type microparticles is applied to products, which are used in an indoor environment having a low illuminance, such as ceilings, walls, floors, furniture and home electric appliances in the interior. In addition, since the tungsten oxide type microparticles exert the antibacterial performance in a dark place, practical antibacterial performance can be obtained even when they are applied to stationery and kitchen goods which are often kept on a shelf or in a drawer.

It is preferable that the tungsten oxide type microparticles used for the antibacterial material have an antibacterial activity value R of 0.3 or more, and 1 or more. It is more preferable that the antibacterial activity value R is 2 or more. By using the tungsten oxide type microparticles satisfying the above conditions, a material having much higher antibacterial performance can be realized. The antibacterial activity value $R_D$ to be evaluated in a dark place is also 0.3 or more, and preferably 1 or more. The antibacterial activity value $R_D$ is more preferably 2 or more. A material using the above tungsten oxide type microparticles can exert high antibacterial performance without being influenced by an illuminance in the used environment.

The above-described materials having the antibacterial properties can be obtained by controlling the grain diameter (specific surface area), crystalline structure, etc. of the tungsten oxide type microparticles. The microparticles used for the antibacterial material is not limited to the microparticles of tungsten oxide but may be microparticles of a tungsten oxide complex. The tungsten oxide complex has a transition metal element and another metal element contained in the main component tungsten oxide. The transition metal elements are elements with atomic numbers 21 to 29, 39 to 47, 57 to 79, and 89 to 109. The tungsten oxide complex preferably contains at least one metal element selected from among Ti, Zr, Mn, Fe, Pd, Pt, Cu, Ag, Zn, Al and Ce. At least one kind of metal element selected from among Cu, Ag and Zn is effective and can improve the antibacterial performance when used in a small amount.

It is preferable that the contained amount of metal element such as a transition metal element in the tungsten oxide complex is determined to be in a range of 0.001 to 50 mass %. When the contained amount of metal element exceeds 50 mass %, the properties as the antibacterial material might be lowered. The contained amount of metal element is more preferably 10 mass % or less, and still more preferably 2 mass % or less. The lower limit value of the contained amount of metal element is not particularly restricted, but its contained amount is 0.001 mass % or more, and more preferably 0.01 mass % or more. The contained amount of at least one metal element selected from among Cu, Ag and Zn is preferably in a range of 0.001 to 1 mass % considering the effects of the tungsten oxide microparticles and the effect of adding the metal element.

In the tungsten oxide complex used for the antibacterial material, the metal element can be existed in various forms. The tungsten oxide complex can contain the metal element in a form such as a single metal element, a compound containing a metal element (compound containing oxide), a complex compound with tungsten oxide, or the like. The metal element contained in the tungsten oxide complex may form a compound with another element by itself. A typical form of the metal element is an oxide. The metal element is mixed in a form of a single element, a compound or a complex compound with, for example, tungsten oxide powder. The metal element may be supported on the tungsten oxide.

As a specific example of the tungsten oxide complex, there is a mixed powder containing copper oxide powder in a range of 0.01 to 5 mass %. It is preferable that the metal oxide powders (titanium oxide powder, iron oxide powder, etc.) other than the copper oxide powder are contained in a range of 0.01 mass % or more and 5 mass % or less into the tungsten oxide complex. The tungsten oxide complex may contain a tungsten compound, e.g., tungsten carbide, other than an oxide. The tungsten carbide is mixed in a powder form in a range of 0.01 mass % or more and 5 mass % or less with the tungsten oxide powder.

The method of combining the tungsten oxide and the metal element (specifically, a single element, a compound or a complex compound of at least one element selected from among Ti, Zr, Mn, Fe, Pd, Pt, Cu, Ag, Zn, Al and Ce) is not particularly limited, and various combining methods such as a mixing method for mixing powders, an impregnation method, a supporting method and the like can be applied. A typical combining method is described below. As a method of combining copper and tungsten oxide, there is a method of mixing tungsten oxide powder and copper oxide powder. There is also an effective method including adding tungsten oxide powder to an aqueous solution or an ethanol solution of copper nitrate or copper sulfate for mixing, drying at a temperature of 70 to 80 degrees C. and then firing at a temperature of 500 to 550 degrees C.

And, it is also possible to apply a method (impregnation method) including dispersing tungsten oxide powder in an aqueous solution of copper chloride or an aqueous solution of copper sulfate, and drying the dispersion liquid. The impregnation method is not limited to the copper combining method but can also be applied to an iron combining method using an aqueous solution of iron chloride, a silver combining method using an aqueous solution of silver chloride, a platinum combining method using an aqueous solution of chloroplatinic acid, a palladium combining method using an aqueous solution of palladium chloride, and the like. In addition, an oxide sol such as a titanium oxide sol or an alumina sol may be used to combine tungsten oxide and a metal element (oxide). Various combining methods can be applied other than the above.

The tungsten oxide type microparticles used for the antibacterial material preferably have an average particle size (D50) in a range of 1 to 200 nm as an average primary particle size. And, the tungsten oxide microparticles have preferably a BET specific surface area in a range of 4.1 to 820 $m^2/g$. The average particle size is determined based on the average particle size (D50) of the accumulated diameter on a volumetric basis of particles in n=50 or more according to image analysis of SEM or TEM photographs. The average particle size (D50) may become consistent with an average grain diameter converted from a specific surface area.

The performance of the antibacterial microparticles improves when a specific surface area is large and a grain diameter is small. When the tungsten oxide type microparticles have an average primary particle size exceeding 200 nm or a BET specific surface area of less than 4.1 $m^2/g$, it becomes difficult to form a uniform and stable film, and satisfactory antibacterial performance might not be obtained. Meanwhile, when the tungsten oxide type microparticles have an average primary particle size of less than 1 nm or a BET specific surface area of exceeding 820 $m^2/g$, the particles become excessively small and handling property (handling property as powder) is inferior. Therefore, the usefulness of the antibacterial material (microparticles) decreases. It is more preferable that the tungsten oxide type microparticles have a BET specific surface area in a range of 8.2 to 410 $m^2/g$ and an average primary particle size in a range of 2 to 100 nm.

The tungsten oxide type microparticles have an average primary particle size of preferably in a range of 2.7 to 75 nm, and more preferably in a range of 5.5 to 51 nm. The BET specific surface area is preferably in a range of 11 to 300 $m^2/g$, and more preferably in a range of 16 to 150 $m^2/g$. In a case where the tungsten oxide type microparticles are used for an antibacterial paint or in a form kneaded into a base material, dispersibility of the particles decreases if the particle size is excessively small. To improve the above point, it is preferable to use the tungsten oxide type microparticles having an average primary particle size of 5.5 nm or more.

The tungsten oxide which constructs the tungsten oxide microparticles or the tungsten oxide complex microparticles has preferably at least one crystalline structure selected from monoclinic crystal and triclinic crystal of tungsten trioxide or a crystalline structure that orthorhombic crystal is mixed in which at least one selected from the monoclinic crystal and the triclinic crystal. The tungsten oxide microparticles or tungsten oxide complex microparticles using the tungsten oxide having the above crystalline structure can stably exert excellent antibacterial performance. It is difficult to identify the presence ratio of individual crystalline phases of the tungsten trioxide, but if the following conditions (1) and (2) are satisfied by measuring by the X-ray diffraction method, it can be estimated that it has the above-described crystalline structure.

In the X-ray diffraction chart (1), 2θ has a first peak (diffraction peak with maximum intensity among all peaks), a second peak (diffraction peak with the second large intensity), and a third peak (diffraction peak with the third large intensity) in a range of 22.5 to 25 degrees.

In the X-ray diffraction chart (2), when it is assumed that a peak having 2θ in a range of 22.8 to 23.4 degrees is A, a peak having 2θa in a range of 23.4 to 23.8 degrees is B, a peak having 2θa in a range of 24.0 to 24.25 degrees is C, and a peak having 2θa in a range of 24.25 to 24.5 degrees is D, the intensity ratio (A/D) of the peak A to the peak D and the intensity ratio (B/D) of the peak B to the peak D each are in a range of 0.5 to 2.0, and the intensity ratio (C/D) of the peak C to the peak D is in a range of 0.04 to 2.5.

X-ray diffraction measurement and analysis are described below. It is determined that the X-ray diffraction measurement is conducted using a Cu target and a Ni filter, smoothing treatment and background removal only are performed such that analysis is not affected by a difference in processing conditions, and the peak intensity is measured without removing Kα2. Here, to read the peak intensity in individual 2θ ranges of the X-ray diffraction chart, it is determined that when a mountain part is clear, a high position of the mountain part is determined as a peak, and its height is read. It is determined that when the mountain part is not clear but it has a shoulder portion, the shoulder portion is determined as a peak in that range, and the height of the shoulder portion is read. If a slope does not have a mountain part or a shoulder portion, the height at the middle of that range is read and determined as peak intensity in that range.

When the tungsten oxide type microparticles have a low crystallinity or a very small particle size, 2θ in the X-ray diffraction chart might become a broad peak having one or two peaks in a range of 22.5 to 25 degrees. The tungsten oxide type microparticles exhibiting the above X-ray diffraction results are not excluded. Antibacterial performance can be provided by using the above tungsten oxide type microparticles.

By using the tungsten oxide type microparticles having the particle size (specific surface area) and the crystalline structure described above, a material exhibiting the antibacterial performance can be realized without requiring irradiation of special light. Practical antibacterial performance can be obtained even in an environment having a low illuminance by applying the above antibacterial material to products, which are used in an indoor environment having a low illuminance, such as indoor ceilings, walls, floors, furniture and home electric appliances. In addition, since the antibacterial material of this embodiment exerts the antibacterial performance even in a dark place, practical antibacterial performance can be obtained even when it is applied to stationery and kitchen goods which are often kept on a shelf or in a drawer.

In addition, the tungsten oxide type microparticles used for antibacterial materials have preferably an antibacterial activity value $R_L$ of 1.0 or more when the antibacterial materials have undergone the evaluation test with visible light irradiated to the above-described test piece. It is determined that the antibacterial property evaluation test under irradiation of visible light is performed by a method according to Fine ceramics—Test method for antibacterial activity of photocatalytic products under photoirradiation and efficacy of JIS-R-1702 (2006). Similar to the above-described antibacterial property evaluation test, the test piece is prepared by adhering the tungsten oxide type microparticles in a range of 0.02 to 40 mg/cm². As bacteria, there is used at least one selected from among *Staphylococcus aureus, Escherichia coli, Klebsiella pneumoniae, Pseudomonas aeruginosa*, methicillin-resistant *Staphylococcus aureus*, and enterohemorrhagic *Escherichia coli*.

The test piece is irradiated with visible light with a wavelength of 380 nm or more and an illuminance of 6000 lx using a white fluorescent lamp and a UV cut filter. The antibacterial property evaluation test is performed under irradiation of the visible light to the test piece. In the antibacterial property evaluation test under irradiation of visible light, the test piece onto which the microparticles are coated is measured for an average value (number) $C_L$ of viable cell count after storing under irradiation of visible light for 24 hours, and an untreated test piece is measured for an average value (number) $B_L$ of viable cell count after storing under irradiation of visible light for 24 hours. The antibacterial activity value $R_L$ is determined based on the following equation (3) from the average values $C_L$ and $B_L$ of viable cell count.

$$R_L = \log(B_L/C_L) \tag{3}$$

Generally, the visible light denotes light having a wavelength in a range of 380 nm to 830 nm. To evaluate the performance in a visible light area, it is determined to use visible light having a wavelength of 380 nm or more only in the evaluation of this embodiment. Specifically, the evaluation is preferably performed by using as a light source a white fluorescent lamp specified by IS-Z-9112 and a UV cut filter which cuts light having a wavelength of less than 380 nm, and irradiating visible light having a wavelength of 380 nm or more only. As the white fluorescent lamp, for example, FL20SS•W/18 manufactured by Toshiba Lighting and Technology Corporation or its equivalent product is used. As the UV cut filter, for example, CLAREX N-169 (trade name) manufactured by Nitto Jushi Kogyo Kabushiki Kaisha or its equivalent product is used.

It is known that tungsten oxide has a photocatalytic action. By satisfying the above-described grain diameter (specific surface area) and crystalline structure and improving the crystallinity of tungsten oxide and tungsten oxide complex, the tungsten oxide type microparticles used for the antibacterial material of this embodiment exhibit antibacterial performance even under no irradiation of light and also exhibit much better antibacterial performance under irradiation of light in a visible light area. For example, as to the peak intensity ratio in the above-described X-ray diffraction chart, when the intensity ratio (A/D) of the peak A to the peak D and the intensity ratio (B/D) of the peak B to the peak D each are in a range of 0.7 to 2.0 and the intensity ratio (C/D) of the peak C to the peak D is in a range of 0.5 to 2.5, the photocatalytic activity becomes high, and much better antibacterial performance can be exerted.

For a titanium oxide based photocatalyst, visible-light responsivity can be improved by doping nitrogen or sulfur to enhance the visible light absorption performance. In addition, a heat treatment temperature is controlled to improve crystallinity or a metal is supported to prevent recombination of electrons and holes, and the photocatalytic activity can be enhanced. But, titanium oxide which exerts high performance under a very high illuminance lowers its performance as the illuminance lowers, and one exhibiting practical photocatalytic performance under a common low illuminance of about 150 to 500 lx has not been obtained.

The tungsten oxide type microparticles composing the antibacterial material have an antibacterial activity value $R_L$ of preferably 3 or more and more preferably 4 or more. A material having high antibacterial properties exhibits good antibacterial activity value $R_{L6h}$ even by the evaluation test conducted after the storage under irradiation of visible light (wavelength: 380 nm or more) having an illuminance of 6000 lx for six hours. The tungsten oxide type microparticles have preferably an antibacterial activity value $R_{L6h}$ of 2 or more. In addition, the tungsten oxide type microparticles have preferably an antibacterial activity value $R_{L1000}$ of 2 or more based on the evaluation test conducted after the storage under irradiation of visible light (wavelength: 380 nm or more) having an illuminance of 1000 lx for 24 hours.

By using the tungsten oxide type microparticles satisfying the above-described conditions, it becomes possible to obtain a material having much higher antibacterial performance in a normal indoor environment. Here, the visible light irradiated to the antibacterial material is not only the light from the above-described white fluorescent lamp but may also be light from a light source such as sunlight, a white LED, a bulb, a halogen lamp or a xenon lamp for general illumination, a blue light emitting diode, a blue laser or the like. In addition, it becomes possible to exert much higher antibacterial performance by irradiating visible light having a high illuminance to the antibacterial material.

It is considered that the antibacterial material of this embodiment exerts antibacterial performance regardless of the presence or not of irradiation of light because a contact area with bacteria is increased by increasing the specific surface area of the tungsten oxide type microparticles, but a mechanism of an antibacterial action exerted in a dark place is not necessarily clear. In addition, the antibacterial performance increases under irradiation of visible light because the contact area with the bacteria is increased by increasing the specific surface area of the tungsten oxide type microparticles, so that an active site can be increased, and a probability of recombination of electrons and holes is decreased by the improvement of crystallinity.

Tungsten oxide has a bandgap of 2.5 to 2.8 eV which is smaller than that of titanium oxide, so that it absorbs visible light. Therefore, excellent visible-light responsivity can be realized. In addition, since a typical crystalline structure of tungsten oxide is a $ReO_3$ structure, a crystal plane with high reaction activity having oxygen is apt to be exposed on the outermost surface layer. Therefore, high hydrophilicity is exerted by adsorbing water. Otherwise, OH radicals are produced by oxidizing the adsorbed water, and molecules and compounds can be oxidized, so that photocatalytic performance better than those of anatase and rutile crystal of titanium oxide can be exerted. In addition, the tungsten oxide type microparticles according to this embodiment have excellent dispersibility because a zeta potential in an aqueous solution having pH 1 to 7 is minus. Therefore, they can be coated thin and uniformly on the base material or the like.

The tungsten oxide type microparticles (powder) used for the antibacterial material may contain metal elements as impurities. The contained amount of the metal elements as impurity elements is preferably 2 mass-% or less. The impurity metal elements include those generally contained in tungsten ores, pollution elements which are mingled while a tungsten compound or the like used as the raw material is produced, and the like. Their examples are Fe, Mo, Mn, Cu, Ti, Al, Ca, Ni, Cr, and Mg. When these elements are used as the constituent elements of the complex, they are not exclusively limited.

The tungsten oxide type microparticles (powder) used for the antibacterial material according to the embodiments of the invention are preferably produced by the following method but it is not limited exclusively. The tungsten oxide type microparticles are preferably produced by applying a sublimation process. It is also effective to add a heat treatment process to the sublimation process. By the tungsten trioxide microparticles produced by the above method, the above-described average primary particle size, BET specific surface area, and crystalline structure can be realized stably. In addition, microparticles (fine powder) having an average primary particle size which approximates to a value converted from the BET specific surface area and small variation in the grain diameter can be provided stably.

First, the sublimation process is described. The sublimation process is a process to obtain the tungsten trioxide microparticles by sublimating a metallic tungsten powder, a tungsten compound powder or a tungsten compound solution in an oxygen atmosphere. The sublimation is a phenomenon that a state change occurs from a solid to gas or gas to solid phase without via a liquid phase. A tungsten oxide powder in a state of microparticles can be obtained by oxidizing a metallic tungsten powder, a tungsten compound powder, or a tungsten compound solution as the raw material while sublimating.

For the raw material (tungsten raw material) of the sublimation process, any of the metallic tungsten powder, tungsten compound powder, and tungsten compound solution may be used. Examples of the tungsten compound used as the raw material include tungsten trioxide ($WO_3$), tungsten dioxide ($WO_2$), tungsten oxide such as lower oxide, tungsten carbide, ammonium tungstate, calcium tungstate, tungstic acid and the like.

By performing the sublimation process of the above-described tungsten raw material in an oxygen atmosphere, metallic tungsten powder or tungsten compound powder is instantaneously changed from a solid to gas phase, and the metallic tungsten steam in the gas phase is oxidized to obtain tungsten oxide microparticles. Even when a solution is used, it becomes a gas phase through tungsten oxide or a compound. Thus, the tungsten oxide microparticles can be obtained by using the oxidation reaction in the gas phase. In addition, the crystalline structure of the tungsten oxide microparticles can be controlled.

As the raw material used in the sublimation process, it is preferable to use at least one selected from among metallic tungsten powder, tungsten oxide powder, tungsten carbide powder, and ammonium tungstate powder because impurities are not easily contained in the tungsten oxide microparticles obtained by sublimating in an oxygen atmosphere. The metallic tungsten powder or tungsten oxide powder is particularly preferable as the raw material in the sublimation process because nothing harmful is contained as a by-product (substance other than tungsten oxide) produced in the sublimation process.

As the tungsten compound used for the raw material, a compound containing tungsten (W) and oxygen (O) as its constituent elements is preferable. When W and O are contained as the constituent elements, sublimation is readily caused instantaneously when a later-described inductively-coupled plasma processing or the like is applied in the sublimation process. Examples of the above tungsten compound include $WO_3$, $W_{20}O_{58}$, $W_{18}O_{49}$, $WO_2$ and the like. And, a solution or salt of tungstic acid, ammonium paratungstate, ammonium metatungstate is also effective.

To produce the tungsten oxide complex microparticles, a transition metal element and another element may be mixed in a form of metal, oxide-containing compound, complex compound or the like in addition to the tungsten raw material. Complex compound microparticles of a composite oxide of tungsten oxide and another element can be obtained by processing the tungsten oxide together with another element at the same time. The tungsten oxide complex microparticles can also be obtained by mixing and supporting the tungsten oxide microparticles with free particles or compound particles of another metal element. A combining method of tungsten oxide and another metal element is not particularly limited, and it is possible to apply various known methods.

It is preferable that the metallic tungsten powder or the tungsten compound powder as the tungsten raw material has an average particle size in a range of 0.1 to 100 μm. The tungsten raw material has an average particle size of more preferably 0.3 μm to 10 pin, much more preferably 0.3 μm to 3 μm, and desirably 0.3 μm to 1.5 μm. When the metallic tungsten powder or the tungsten compound powder having an average particle size in the above-described range is used, sublimation tends to occur.

When the tungsten raw material has an average particle size of less than 0.1 μm, it is not desirable industrially because the raw material powder is excessively fine, so that the raw material powder must be adjusted previously, its handling property lowers, and it costs high. When the tungsten raw material has an average particle size of more than 100 μm, a uniform sublimation reaction becomes hard to occur. Even if the average particle size is large, the uniform sublimation reaction can be caused by processing by a large amount of energy, but it is not desirable industrially.

Examples of the method to sublimate the tungsten raw material in an oxygen atmosphere by the sublimation process include at least one processing selected from among inductively-coupled plasma processing, arc discharge processing, laser processing, electron beam processing, and gas burner processing. Among them, the laser processing or the electron beam processing irradiates laser or electron beam to perform the sublimation process. Since the laser or the electron beam has a small irradiation spot diameter, it takes time when a large amount of raw material is processed at a time but it has an advantage that it is not necessary to strictly control the grain diameter of raw material powder and the stability of the supply amount.

The inductively-coupled plasma processing and the arc discharge processing require that the generation area of a plasma discharge and an arc discharge must be adjusted, but the oxidation reaction of a large amount of raw material powder can be caused in an oxygen atmosphere. And, the amount of the raw material which can be processed at a time can be controlled. The gas burner processing is relatively low in power cost, but it is hard to process the raw material powder or the raw material solution in a large amount. Therefore, the gas burner processing is inferior in terms of productivity. The gas burner processing is appropriate when it has energy sufficient to cause sublimation, and not limited particularly. A propane gas burner and an acetylene gas burner are used.

In a case where the inductively-coupled plasma processing is applied to the sublimation processing, there is used a method that argon gas or oxygen gas is normally used to generate plasma and metallic tungsten powder or tungsten compound powder is supplied into the plasma. Examples of the method of supplying the tungsten raw material into the plasma include a method of blowing in metallic tungsten powder or tungsten compound powder together with carrier gas, a method of blowing in a dispersion liquid which has the metallic tungsten powder or the tungsten compound powder dispersed into a predetermined liquid dispersion medium.

Examples of the carrier gas which is used when metallic tungsten powder or tungsten compound powder is blown into the plasma include air, oxygen, oxygen-containing inert gas, etc. Among them, air is preferably used because its cost is low. In a case where oxygen is sufficiently contained in a reactive site, such as when oxygen-containing reaction gas is flown in other than the carrier gas or when the tungsten compound powder is tungsten trioxide, inert gas such as argon or helium may be used as the carrier gas. It is preferable to use oxygen, oxygen-containing inert gas or the like as the reaction gas. When the oxygen-containing inert gas is used, the oxygen amount is preferably determined such that the oxygen amount required for the oxidation reaction can be supplied sufficiently.

The crystalline structure of the tungsten trioxide microparticles can be controlled readily by applying a method of blowing in metallic tungsten powder or tungsten compound powder together with the carrier gas and adjusting a gas flow rate, a pressure in the reaction vessel or the like. Specifically, tungsten trioxide microparticles having a crystalline structure of at least one (monoclinic crystal, triclinic crystal, or mixed crystal of monoclinic crystal and triclinic crystal) selected from monoclinic crystal and triclinic crystal or a crystalline structure in which orthorhombic crystal is mixed with the above can be obtained readily. It is more preferable that the crystalline structure of the tungsten trioxide microparticles is a mixed crystal of monoclinic crystal and triclinic crystal or a mixed crystal of monoclinic crystal, triclinic crystal and orthorhombic crystal.

As the dispersion medium used for the production of the dispersion liquid of metallic tungsten powder or tungsten compound powder, there is a liquid dispersion medium having an oxygen atom in molecules. When the dispersion liquid is used, handling of the raw material powder becomes easy. As the liquid dispersion medium having the oxygen atom in the molecules, there is used, for example, one containing 20 volume % of more of at least one selected from water and alcohol. Examples of the alcohol used as the liquid dispersion medium are preferably at least one selected from among methanol, ethanol, 1-propanol and 2-propanol. Since water and alcohol are apt to be volatilized by heat from plasma, they do not hinder the sublimation reaction or oxidation reaction of the raw material powder, and tend to promote the oxidation reaction because oxygen is contained in the molecules.

In a case where the dispersion liquid is produced by dispersing metallic tungsten powder or tungsten compound powder into a dispersion medium, the metallic tungsten powder or the tungsten compound powder is preferably contained in a range of 10 to 95 mass % into the dispersion liquid, and more preferably in a range of 40 to 80 mass %. By dispersing in such a range into the dispersion liquid, the metallic tungsten powder or the tungsten compound powder can be dispersed uniformly into the dispersion liquid. When dispersed uniformly, a sublimation reaction of the raw material powder tends to occur uniformly. If the contained amount in the dispersion liquid is less than 10 mass %, the amount of raw material powder is too small to produce efficiently. If it exceeds 95 mass %, the dispersion liquid is small, the viscosity of the raw material powder increases and tends to adhere to the vessel, and the handling property is decreased.

The crystalline structure of the tungsten trioxide microparticles can be controlled easily by applying a method of preparing a dispersion liquid of metallic tungsten powder or tungsten compound powder and blowing into plasma. Specifically, tungsten trioxide microparticles having a crystalline structure of at least one selected from monoclinic crystal and triclinic crystal or a crystalline structure in that orthorhombic crystal is mixed with it can be obtained easily. In addition, by using a tungsten compound solution as a raw material, the sublimation reaction can be caused uniformly, and controllability of the crystalline structure of the tungsten trioxide microparticles is improved. The above-described method of using the dispersion liquid can also be applied to arc discharge processing.

In a case where the sublimation process is performed by irradiating the laser or the electron beam, it is preferable that metallic tungsten or a tungsten compound formed into a pellet form is preferably used as the raw material. Since the laser or the electron beam has a small irradiation spot diameter, it becomes difficult to supply when metallic tungsten powder or tungsten compound powder is used, but sublimation can be caused efficiently by using the pelletized metallic tungsten or tungsten compound. The laser is adequate when it has energy enough to sublimate the metallic tungsten or the tungsten compound and not particularly limited, but $CO_2$ laser is preferable because it has high energy.

When at least either one of the pellets or the irradiation source of the laser light or the electron beam is moved to irradiate the laser or the electron beam to the pellets, the entire surface of the pellets having a certain size can be sublimated effectively. Thus, it becomes easy to obtain a tungsten trioxide powder having a crystalline structure in that the orthorhombic crystal is mixed in at least one selected from monoclinic crystal and triclinic crystal. The above-described pellets can also be applied to inductively-coupled plasma processing and arc discharge processing.

The tungsten oxide type microparticles used for antibacterial material of this embodiment can be obtained by the above-described sublimation process only, but the tungsten oxide type microparticles produced by the sublimation process can be subject to a heat treatment process. The heat treatment process performs heat treatment of the tungsten trioxide microparticles obtained by the sublimation process in an oxidizing atmosphere at a prescribed temperature for a prescribed time. Even when the tungsten trioxide microparticles cannot be formed sufficiently because of the condition control or the like of the sublimation process, the ratio of the tungsten trioxide microparticles in the tungsten oxide microparticles can be set to 99% or more, and substantially 100% by performing the heat treatment. The crystalline structure of the tungsten trioxide microparticles can be adjusted to a prescribed structure by the heat treatment process.

As the oxidizing atmosphere used in the heat treatment process, there are, for example, air and oxygen-containing gas. The oxygen-containing gas means an inert gas containing oxygen. The heat treatment temperature is preferably in a range of 200 to 1000 degrees C., and more preferably 400 to 700 degrees C. The heat treatment time is preferably 10 minutes to 5 hours, and more preferably 30 minutes to 2 hours. Tungsten trioxide can be formed readily from tungsten oxide other than tungsten trioxide by setting the temperature and time for the heat treatment process to the above-described range. And, to obtain powder with less defects and good crystallinity, it is preferable that the temperature is gradually raised and lowered in the heat treatment. Sudden heating and quenching in the heat treatment result in degradation of crystallinity.

When the heat treatment temperature is less than 200 degrees C., an oxidation effect for changing the powder which did not become tungsten trioxide in the sublimation process into tungsten trioxide might not be obtained sufficiently. When the heat treatment temperature exceeds 1000 degrees C., the tungsten oxide microparticles grow suddenly, so that the specific surface area of the obtained tungsten oxide fine powder tends to decrease. In addition, when the heat treatment process is performed with the above-described temperature and time, it becomes possible to adjust the crystalline structure and crystallinity of the tungsten trioxide fine powder.

The antibacterial material of this embodiment can be applied to various antibacterial members and antibacterial products. The antibacterial material is used in a form that the tungsten oxide type microparticles produced by the above-described production method are adhered to the surface of a base material or kneaded into a base material. Examples of a method of adhering the tungsten oxide type microparticles to the surface of the base material include a method that a dispersion liquid or paint having the tungsten oxide type microparticles dispersed in a dispersion medium such as water or alcohol is coated on the surface of the base material. An antibacterial member having a film (antibacterial film) such as a coating or a coated film containing the tungsten oxide type microparticles can be obtained by applying the above method.

The antibacterial film preferably contains the antibacterial material (tungsten oxide type microparticles) in a range of 0.1 to 90 mass %. If the contained amount of the antibacterial material is less than 0.1 mass %, there is a possibility that the antibacterial performance might not be obtained fully. If the contained amount of the antibacterial material exceeds 90 mass %, there is a possibility that the properties of the film are degraded. It is preferable that the antibacterial film has thickness in a range of 2 to 1000 nm. If the thickness is less than 2 nm, the amount of the antibacterial material is in shortage, and there is a possibility that the antibacterial performance cannot be obtained sufficiently. If the antibacterial film has thickness exceeding 1000 nm, the antibacterial performance can be obtained, but the strength as the film is apt to become low. It is more preferable that the antibacterial film has thickness in a range of 2 to 400 nm.

The antibacterial film may contain an inorganic binder or the like other than the antibacterial material using the tungsten oxide type microparticles. Examples of the inorganic binder include at least one element selected from among amorphous oxides of Si, Ti, Al, W and Zr. To use the inorganic binder including an amorphous oxide, for example, it is added as colloidal silica, alumina sol, titania sol, zirconia sol or the like into a paint using the tungsten oxide type microparticles. The contained amount of the inorganic binder is preferably in a range of 5 to 95 mass %. There is a possibility that the desired antibacterial performance cannot be obtained if the amount of the inorganic binder contained in the antibacterial film exceeds 95 mass %. Sufficient bonding power cannot be obtained if the contained amount of the inorganic binder is less than 5 mass %.

The antibacterial member of this embodiment include the above-described antibacterial material and antibacterial film. Specific examples of the antibacterial member include a member which has an antibacterial material added to or impregnated into a base material, a member which has a dispersion liquid or a paint containing the antibacterial material coated onto a base material, and the like. The antibacterial material may be used by performing mixing, supporting or impregnating of the tungsten oxide particles with a material having adsorption performance such as activated carbon or zeolite. The antibacterial film and antibacterial member can be used under irradiation of visible light having an illuminance of 1000 lx or less and even in a dark place. The antibacterial material, the antibacterial film and the antibacterial member are used to be antibacterial against at least one bacterium selected from among *Staphylococcus aureus, Escherichia coli, Klebsiella pneumoniae, Pseudomonas aeruginosa*, methicillin-resistant *Staphylococcus aureus* (MRSA), and enterohemorrhagic *Escherichia coli* (O157).

Products using the antibacterial material, the antibacterial film and the antibacterial member are those which are required to have antibacterial properties, such as air conditioners, air cleaners, electric fans, refrigerators, microwave ovens, dishwashing and drying machines, rice cookers, pots, pot lids, IH heaters, washing machines, vacuum cleaners, lighting equipment (lamps, equipment bodies, shades, etc.), hygiene goods, toilets, washbasins, mirrors, bathrooms (walls, ceilings, floors, etc.), building materials (interior walls, ceiling materials, floors, exterior walls, etc.), interior goods (curtains, carpets, tables, chairs, sofas, shelves, beds, beddings, etc.), glass, sashes, handrails, doors, knobs, clothes, filters used for home electric appliances and the like, stationery, kitchen goods, members used in automotive interiors, etc. Examples of the base material include glass, ceramics, plastics, resins such as acryl, etc., paper, textiles, metal, wood, and the like. When the products are resins and textiles, coating, adhesion or kneading can be applied.

The antibacterial material, antibacterial film and antibacterial member of this embodiment exhibit practical antibacterial performance regardless of light irradiation. Thus, even when they are used in a place not readily illuminated with light, a place with a low illuminance, or particularly in a living space or an automobile interior, antibacterial performance can be obtained. In the automobile interior, the antibacterial performance can be exerted even at night with low light. Practical antibacterial performance can be exerted stably without degradation in performance due to a change in quality different from the antibacterial agent using the conventionally used antibacterial metal ions.

EXAMPLES

Example 1

Tungsten oxide microparticles were produced by heating an ammonium tungstate at 900 degrees C. in the atmosphere for two hours, and pulverizing by a ball mill. The obtained tungsten oxide microparticles were measured for an average primary particle size (D50) and a BET specific surface area. The average primary particle size was measured by image analysis of TEM photograph. For TEM observation, H-7100FA manufactured by Hitachi, Ltd. was used, magnified photographs were subjected to image analysis to extract 50 or more particles, an integrated diameter on a volumetric basis was determined, and D50 was calculated. The BET specific surface area was measured by using a specific surface area analyzer Macsorb1201 manufactured by Mountech Co., Ltd. A pretreatment was performed in nitrogen under conditions of 200 degrees C. and 20 minutes. Measured results of the average particle size (D50) and the BET specific surface area are shown in Table 1.

And, X-ray diffraction of tungsten oxide powder was performed. The X-ray diffraction was performed by using an X-ray diffractometer RINT-2000 manufactured by Rigaku Corporation, a Cu target, a Ni filter, and a graphite (002) monochrometer. Measuring conditions include a tube voltage: 40 kV, a tube current: 40 mA, a divergence slit: ½ degree, a scattering slit: auto, a receiving slit: 0.15 mm, 20 measuring range: 20 to 70 degrees, a scanning rate: 0.5 degree/min, and a sampling width: 0.004 degree. Before the peak intensity is measured, smoothing and background removal processing only were performed without removing Kα2. For smoothing, a Savizky-Golay (least-square method) was used, and a filter point was set to 11. The background removal was performed within a measuring range with a linear fit, and a threshold value σ3.0. Crystalline structure identification results of the tungsten oxide microparticles based on the X-ray diffraction results are shown in Table 1.

Then, the obtained tungsten oxide microparticles were measured for antibacterial performance. First, the tungsten oxide microparticles were mixed with water and underwent an ultrasonic dispersion process to produce a dispersion liquid. The dispersion liquid was spread on a glass plate of 5×5 cm, and dried at 200 degrees C. for 30 minutes to produce a sample on which 0.05 g of the tungsten oxide microparticles were coated. The adhered amount of the tungsten oxide microparticles was 2 mg/cm². The test piece was evaluated for the antibacterial performance by a method according to Antimicrobial products—Test for antimicrobial activity of JIS-Z-2801 (2000) to determine an antibacterial activity value R. The antibacterial activity value R was determined as an average value of three evaluation tests. The evaluation method is as follows.

*Staphylococcus aureus* was used as test bacteria for antibacterial performance. In the surfaces of the test piece and an untreated test piece (glass plate) to be evaluated, $5 \times 10^5$ bacteria were inoculated, the individual surfaces were covered with a film, and the test pieces were kept under conditions of 35±1 degrees C. and a relative humidity of 90% for 24 hours. After the storage, the bacteria adhered to the film were washed out, the resultant liquid was used and cultured for 48 hours, and the number of bacteria was measured. The antibacterial activity value R was determined from the viable cell count (average value (number) of three times) $C_1$ after the test piece to which the tungsten oxide microparticles were adhered was stored for 24 hours, and the viable cell count (average value (number) of three times) $B_1$ after the 24-hour storage of the untreated test piece. In addition, the antibacterial performance was evaluated in the same manner as the above except that the 24-hour storage was performed in a dark place to determine an antibacterial activity value $R_D$. The antibacterial activity value R and the antibacterial activity value $R_D$ are shown in Table 2.

In addition, an antibacterial activity value $R_L$ of the test piece was determined by evaluating the antibacterial performance in the same manner as the above-described method except that a white fluorescent lamp and an UV cut filter were used, and 24-hour storage was conducted while irradiating visible light having a wavelength of 380 nm or more and an illuminance of 6000 lx by a method according to Fine ceramics—Test method for antibacterial activity of photocatalytic products under photoirradiation and efficacy of JIS-R-1702 (2006). The antibacterial activity value $R_L$ is shown in Table 2. As the light source, a white fluorescent lamp (FL20SS•ESI/18 manufactured by Toshiba Lighting and Technology Corporation) was used, and a UV cut filter (CLAREX N-169 manufactured by Nitto Jushi Kogvo Kabushiki Kaisha) was used to cut light having a wavelength of less than 380 nm.

Since the tungsten oxide microparticles of Example 1 had a rather large grain diameter, the antibacterial properties were exhibited in a normal test environment and a test environment for storing in a dark place but had a relatively small value. In addition, the antibacterial activity value $R_L$ was 0.6 when stored under irradiation of visible light, and the antibacterial properties were low as the photocatalyst. It is considered that the above results depend on the fact that the tungsten oxide microparticles had a rather large grain diameter, and the contact area with the bacteria became small.

Example 2

Tungsten trioxide powder having an average particle size of 0.5 μm was prepared as the raw material powder. The raw material powder was sprayed together with a carrier gas (Ar) to RF plasma, and oxygen was flown as a reaction gas at a flow rate of 80 L/min. At that time, the pressure in a reaction vessel was adjusted to a low pressure of 25 kPa. Thus, the tungsten oxide microparticles were produced through the sublimation process to execute an oxidation reaction while sublimating the raw material powder. An average particle size (D50), a specific surface area, and a crystalline structure of the obtained tungsten oxide microparticles were measured and evaluated in the same manner as in Example 1. The results are shown in Table 1.

Similar to Example 1, a test piece was produced by coating the tungsten oxide microparticles on a glass plate, and antibacterial performance was evaluated in a normal environment and a dark place and under irradiation of visible light.

Antibacterial activity values $R$, $R_D$, $R_L$ are shown in Table 2. In addition, an antibacterial activity value $R_{L6h}$ which was obtained by storing for six hours under irradiation of visible light having an illuminance of 6000 lx, an antibacterial activity value $R_{D6h}$ which was obtained by storing for six hours in a dark place for comparison with the above, and an antibacterial activity value $R_{L1000}$ which was obtained by storing 24 hours under irradiation of visible light having an illuminance of 1000 lx were measured and evaluated. The results are also shown in Table 2. The tungsten oxide microparticles of Example 2 had antibacterial properties even in a dark place and exhibited an antibacterial activity value of 2 or more under irradiation of visible light.

Examples 3 to 5

Tungsten oxide microparticles were produced by performing the sublimation process in the same manner as in Example 2 except that argon was flown as the reaction gas at a flow rate of 40 L/min, and air was flown at a flow rate of 40 L/min to adjust the pressure in the reaction vessel to 40 kPa. In addition, the tungsten oxide microparticles underwent a heat treatment in the atmosphere under conditions of 500 to 900 degrees C. for 1 to 2 hours. An average particle size (D50), a specific surface area, and a crystalline structure of the obtained tungsten oxide microparticles (Examples 3 to 5) are shown in Table 1.

Antibacterial activity values $R$, $R_D$, $R_L$, $R_{D6h}$, $R_{L6h}$, $R_{L1000}$ of the obtained tungsten oxide microparticles were measured and evaluated in the same manner as in Example 2. The results are shown in Table 2. It was confirmed that the tungsten oxide microparticles of Examples 3 to 5 exhibited an antibacterial activity value of 2 or more in a normal environment and storing in a dark place (24 hours) and exhibited an antibacterial activity value of 3 or more under irradiation of visible light. Especially, Examples 3 and 4 exhibited a high antibacterial activity value of 4.5 or more even when the irradiation time of visible light was short or even in an environment with a low illuminance. It is considered that the particle size was small and the contact area with the bacteria became large. It is considered that Examples 3 to 5 exhibited high antibacterial performance even though the grain diameter was larger than in Example 2, because the crystallinity of the tungsten oxide microparticles was improved, defects and the like were few, and photocatalyst performance was improved.

Here, the number of bacteria has an initial value of about $5 \times 10^5$, and a minimum number of bacteria is less than 10 after the evaluation. When the number of bacteria is less than 10, it is determined to be 10 to calculate an antibacterial activity value, so that a maximum antibacterial activity value becomes 4.7. For evaluation of higher antibacterial performance, it is effective to compare with an antibacterial activity value when a storing time (including storage under irradiation of visible light) is decreased or an antibacterial activity value when storage is made with a low illuminance. The antibacterial performance by the photocatalyst effect can be evaluated by comparing, for example, the number of bacteria obtained when stored for six hours while irradiating visible light having an illuminance of 6000 lx and the number of bacteria obtained when stored in a dark place for six hours.

Example 6

The same sublimation process and heat treatment process as in Example 3 were performed except that tungsten oxide powder with a large amount of impurities such as Fe and Mo is used as raw material and charged to plasma to produce tungsten oxide complex microparticles containing Fe in 300 ppm. The obtained tungsten oxide complex microparticles were measured and evaluated for an average particle size (D50), a specific surface area, and a crystalline structure. The results are shown in Tablet. Similar to Example 1, the test piece was produced by coating the tungsten oxide complex microparticles on a glass plate, and antibacterial performance was evaluated in a normal environment and a dark place and under irradiation of visible light. Antibacterial activity values $R$, $R_D$, $R_L$, $R_{D6h}$, $R_{L6h}$, and $R_{L1000}$ are shown in Table 2. It was confirmed that the tungsten oxide complex microparticles of Example 6 exhibited high antibacterial performance similar to the tungsten oxide microparticles of Example 3 regardless of the normal environment, the dark place, and the irradiation of visible light.

Example 7

The tungsten oxide powder obtained in Example 3 was mixed with 1 mass % of copper oxide (CuO) powder. The obtained tungsten oxide complex powder was measured and evaluated for an average particle size (D50), a specific surface area, and a crystalline structure. The results are shown in Table 1. In addition, the test piece was produced by coating tungsten oxide complex microparticles on a glass plate in the same manner as in Example 1 and evaluated for antibacterial performance in a normal environment and a dark place and under irradiation of visible light. Antibacterial activity values R, $R_D$, $R_L$, $R_{D6h}$, $R_{L6h}$, and $R_{L1000}$ are shown in Table 2. It was confirmed that the tungsten oxide complex microparticles of Example 7 exhibited high antibacterial performance similar to the tungsten oxide microparticles of Example 3 regardless of the normal environment, the dark place, and the irradiation of visible light.

Examples 8 to 13

In Example 8, tungsten oxide complex powder containing 0.1 mass % of zirconium (Zr) was produced by performing the sublimation process and the heat treatment process in the same manner as in Example 3 except that tungsten oxide powder and zirconium oxide powder were mixed and used as raw materials to be charged to plasma.

In Example 9, the tungsten oxide powder obtained in Example 3 was dispersed in an aqueous solution of chloroplatinic acid, visible light was irradiated and methanol was charged to perform supporting by a photodeposition method. Centrifugation was performed to wash twice by removal of the supernatant and addition of water. After the supernatant was removed, the powder was dried at 110 degrees C. for 12 hours to produce tungsten oxide complex powder containing 0.1 mass % of platinum (Pt).

In Example 10, the tungsten oxide powder obtained in Example 3 was dispersed in an aqueous solution of palladium chloride. The dispersion liquid was centrifuged to wash twice by removal of the supernatant and addition of water. After the supernatant was removed, the powder was dried at 110 degrees C. for 12 hours to produce tungsten oxide complex powder containing 0.5 mass % of palladium (Pd).

In Example 11, the tungsten oxide powder obtained in Example 3 was mixed with titanium oxide powder at a ratio of 10 mass % to produce tungsten oxide complex powder.

In Example 12, the tungsten oxide powder obtained in Example 3 was dispersed in an aqueous solution of cerium chloride. The dispersion liquid was centrifuged to wash twice by removal of the supernatant and addition of water. After the supernatant was removed, the powder was dried at 110 degrees C. for 12 hours to produce tungsten oxide complex powder containing 0.1 mass % of cerium (Ce).

In Example 13, the tungsten oxide powder obtained in Example 3 was dispersed in an aqueous solution of manganese chloride. The dispersion liquid was centrifuged to wash twice by removal of the supernatant and addition of water. After the supernatant was removed, the powder was dried at 110 degrees C. for 12 hours to produce tungsten oxide complex powder containing 0.1 mass % of manganese (Mn).

The tungsten oxide complex powders of Examples 8 to 13 were measured and evaluated for an average particle size (D50), a specific surface area, and a crystalline structure. The results are shown in Table 1. Further, test pieces were produced by coating the tungsten oxide complex microparticles on a glass plate in the same manner as in Example 1 and evaluated for antibacterial performance in a normal environment and a dark place and under irradiation of visible light. Antibacterial activity values R, $R_D$, $R_L$, $R_{D6h}$, $R_{L6h}$, and $R_{L1000}$ are shown in Table 2. It was confirmed that all the tungsten oxide complex microparticles of Examples 8 to 13 had high antibacterial performance similar to the tungsten oxide microparticles of Example 3, regardless of the normal environment, the dark place and the visible light irradiation.

Comparative Example 1

Tungsten oxide powder (manufactured by Rare Metallic Co., Ltd.) available on the market as a reagent or the like was used to perform the same measurement and evaluation as in Example 1. Powder properties are shown in Table 1. Further, the tungsten oxide powder was coated on a glass plate in the same manner as in Example 1, but a film could not be formed because the grain diameter was considerably large, and the antibacterial performance could not be evaluated.

Comparative Example 2

Nitrogen doped titanium oxide powder as a visible light-responsive photocatalyst was evaluated for antibacterial performance in the same manner as in Example 1. Powder properties are shown in Table 1, and antibacterial performance is shown in Table 2. When the nitrogen doped titanium oxide powder was stored while visible light having an illuminance of 6000 lx was irradiated for 24 hours, an antibacterial activity value $R_L$ had 2 or more, but it was confirmed that the antibacterial activity value was low in a normal environment and a dark place and under low illuminance, and sufficient antibacterial performance could not be obtained.

TABLE 1

| | POWDER PROPERTIES | | |
|---|---|---|---|
| | Average particle size (D50) [nm] | BET specific surface area [m$^2$/g] | Crystalline structure |
| Example 1 | 222 | 3.7 | Monoclinic crystal |
| Example 2 | 2.2 | 411 | Monoclinic crystal, triclinic crystal, orthorhombic crystal (Low crystallinity) |
| Example 3 | 24 | 33 | Monoclinic crystal, triclinic crystal, orthorhombic crystal |
| Example 4 | 89 | 10 | Monoclinic crystal, triclinic crystal, orthorhombic crystal |
| Example 5 | 195 | 4.2 | Monoclinic crystal, triclinic crystal |
| Example 6 | 22 | 34 | Monoclinic crystal, triclinic crystal, orthorhombic crystal |
| Example 7 | 26 | 30 | Monoclinic crystal, triclinic crystal, orthorhombic crystal |
| Example 8 | 22 | 36 | Monoclinic crystal, triclinic crystal, orthorhombic crystal |
| Example 9 | 26 | 30 | Monoclinic crystal, triclinic crystal, orthorhombic crystal |
| Example 10 | 24 | 33 | Monoclinic crystal, triclinic crystal, orthorhombic crystal |
| Example 11 | 23 | 33 | Monoclinic crystal, triclinic crystal, orthorhombic crystal |
| Example 12 | 23 | 34 | Monoclinic crystal, triclinic crystal, orthorhombic crystal |
| Example 13 | 24 | 32 | Monoclinic crystal, triclinic crystal, orthorhombic crystal |
| Comp. Exam. 1 | 1210 | 0.7 | Monoclinic crystal |
| Comp. Exam. 2 | 10 | 136 | — |

TABLE 2

Antibacterial property evaluation test (Antibacterial activity value)

|  | R (24 h) | $R_D$ (24 h) | $R_L$ (6000lx × 24 h) | $R_{D6h}$ (6 h) | $R_{L6h}$ (6000lx × 6 h) | $R_{L1000}$ (1000lx × 24 h) |
|---|---|---|---|---|---|---|
| Example 1 | 0.4 | 0.3 | 0.6 | — | — | — |
| Example 2 | 1.8 | 1.6 | 2.1 | 0.4 | 2.0 | 1.9 |
| Example 3 | 4.5 | 4.2 | 4.7 | 1.1 | 4.7 | 4.7 |
| Example 4 | 4.3 | 4.0 | 4.7 | 1.0 | 4.5 | 4.5 |
| Example 5 | 3.2 | 2.8 | 3.1 | 0.7 | 2.5 | 2.3 |
| Example 6 | 4.4 | 4.0 | 4.7 | 1.0 | 4.7 | 4.7 |
| Example 7 | 4.5 | 4.4 | 4.7 | 1.1 | 4.7 | 4.7 |
| Example 8 | 4.5 | 4.3 | 4.7 | 1.1 | 4.7 | 4.7 |
| Example 9 | 4.5 | 4.2 | 4.7 | 1.1 | 4.7 | 4.7 |
| Example 10 | 4.4 | 4.0 | 4.7 | 1.0 | 4.7 | 4.7 |
| Example 11 | 4.4 | 4.0 | 4.7 | 1.0 | 4.7 | 4.6 |
| Example 12 | 4.5 | 4.1 | 4.7 | 1.0 | 4.7 | 4.6 |
| Example 13 | 4.5 | 3.9 | 4.7 | 1.0 | 4.7 | 4.7 |
| Comp. Exam. 1 | x | x | x | x | x | x |
| Comp. Exam. 2 | 0.2 | 0.1 | 2.2 | 0.0 | 0.6 | 0.5 | x: Film could not be formed. Evaluation impossible.

Examples 14 to 20

To evaluate films containing tungsten oxide microparticles or tungsten oxide complex microparticles for antibacterial performance, the films were formed by using the microparticles (powders) of Example 1 to Example 7. The individual powders were used to prepare water-based dispersion liquids, which were then coated on a ceramics plate to form the films. The member having the above films of microparticles was cut to produce 5×5 cm test pieces, and they were evaluated for antibacterial performance in the same manner as those of the powders. The results are shown in Table 3.

Comparative Example 3

A member including a film of titanium oxide particles was produced by using a nitrogen-doped type titanium oxide powder to prepare a water-based dispersion liquid and coating it onto a ceramics plate. The member was cut to produce a 5×5 cm test piece, and it was evaluated for antibacterial performance. The results are shown in Table 3.

Examples 21 to 23

In Example 21, a water-based dispersion liquid was produced by adding 5 mass % of the tungsten oxide powder obtained in Example 3 and silver nitrate at a rate of 0.0005 mass % in Ag equivalent, a photoreduction process was performed, and the liquid was coated on a ceramics plate to form a film. The member having the above film was cut to produce a 5×5 cm test piece, and antibacterial performance was evaluated. The results are shown in Table 3.

In Example 22, a water-based paint was prepared by mixing 5 mass-% of the tungsten oxide powder obtained in Example 3 and 0.5 mass % of amorphous $ZrO_2$ and dispersing in water. The water-based paint was coated on a ceramics plate to form a film. The member having the above film was cut to produce a 5×5 cm test piece, and antibacterial performance was evaluated. The results are shown in Table 3.

In Example 23, a water-based paint was prepared by mixing 5 mass % of the tungsten oxide powder obtained in Example 3 and 0.5 mass % of colloidal silica and dispersing in water. The water-based paint was coated on a ceramics plate to form a film. The member having the above film was cut to produce a 5×5 cm test piece, and antibacterial performance was evaluated. The results are shown in Table 3.

Comparative Example 4

An Ag-based antibacterial agent was coated on a ceramics plate. The obtained member was cut to produce a 5×5 cm test piece, and antibacterial performance was evaluated. The results are shown in Table 3.

Comparative Example 5

Colloidal silica was coated on a ceramics plate. The obtained member was cut to produce a 5×5 cm test piece, and antibacterial performance was evaluated. The results are shown in Table 3.

TABLE 3

Antibacterial property evaluation test (Antibacterial activity value)

|  | R (24 h) | $R_D$ (24 h) | $R_L$ (6000lx × 24 h) | $R_{D6h}$ (6 h) | $R_{L6h}$ (6000lx × 6 h) | $R_{L1000}$ (1000lx × 24 h) |
|---|---|---|---|---|---|---|
| Example 14 | 0.4 | 0.3 | 0.5 | — | — | — |
| Example 15 | 1.8 | 1.6 | 2.0 | 0.4 | 1.9 | 1.9 |
| Example 16 | 4.5 | 4.3 | 4.7 | 1.1 | 4.7 | 4.7 |
| Example 17 | 4.3 | 4.1 | 4.7 | 1.0 | 4.5 | 4.4 |
| Example 18 | 3.2 | 2.9 | 3.2 | 0.7 | 2.5 | 2.4 |
| Example 19 | 4.4 | 4.3 | 4.7 | 1.1 | 4.7 | 4.6 |
| Example 20 | 4.5 | 4.4 | 4.7 | 1.1 | 4.7 | 4.7 |
| Example 21 | 4.7 | 4.7 | 4.7 | 1.2 | 4.7 | 4.7 |
| Example 22 | 4.6 | 4.5 | 4.7 | 1.1 | 4.7 | 4.7 |
| Example 23 | 4.4 | 4.2 | 4.7 | 1.1 | 4.6 | 4.7 |
| Comp. Exam. 3 | 0.2 | 0.1 | 2.1 | 0.0 | 0.6 | 0.4 |
| Comp. Exam. 4 | 4.7 | 4.7 | 4.7 | 1.2 | 4.7 | 4.7 |
| Comp. Exam. 5 | 0.0 | 0.0 | 0.0 | 0.0 | 0.0 | 0.0 |

It is apparent from Table 3 that it was confirmed that all the members (members having the antibacterial film) of Examples 14 to 23 show high antibacterial performance similar to the microparticles. Comparative Example 4 showed high antibacterial performance based on the antibacterial effect of Ag but has disadvantages that the Ag-based antibacterial agent costs high and has a possibility of causing metal allergy, a short duration of performance, and the like. Since Comparative Example 5 in which only the colloidal silica was coated does not show antibacterial performance, it is seen that the antibacterial performance provided by the member of Example 23 is based on the tungsten oxide microparticles.

Example 24

To evaluate the sustainability of antibacterial performance, the member of Example 23 was evaluated for antibacterial properties immediately after the film formation and after a six-month storage in a normal environment. The antibacterial activity value R was 4.2 and 4.3 for both cases, and it was confirmed that high antibacterial performance is maintained even after six months.

Comparative Example 6

The member of Comparative Example 4 was evaluated for antibacterial properties immediately after processing the Ag based antibacterial agent and after a six-month storage in a normal environment. The antibacterial activity value R was 4.7 immediately after the sample production, but the antibacterial activity value R dropped to 1.7 after six months. The Ag-based antibacterial agent showed high antibacterial properties in the early stage, but it was confirmed that the antibacterial properties drop with a lapse of time.

Example 25

Antibacterial performance was evaluated in the same manner as in Example 3 except that a sample was produced by coating 0.5 mg of the tungsten oxide powder obtained in Example 3 onto a 5×5 cm glass plate. The adhered amount of the tungsten oxide microparticles was 0.02 mg/cm$^2$. As a result, it was confirmed that the same high antibacterial properties as in Example 3 are shown in the normal environment and the dark place and under irradiation of light. It is assumed that high antibacterial properties could be obtained using a small amount of powder because the tungsten oxide powder has a small grain diameter, and a uniform coated layer can be formed.

As described above, the antibacterial material using the tungsten oxide microparticles or the tungsten oxide complex microparticles and also the film or the member having the antibacterial material can exhibit practical antibacterial performance for a long period regardless of light irradiation. In addition, they show high antibacterial properties even under visible light irradiation having a low illuminance. The above material, film and member were evaluated for antibacterial properties using *Escherichia coli*, *Klebsiella pneumoniae*, *Pseudomonas aeruginosa*, methicillin-resistant *Staphylococcus aureus*, and enterohemorrhagic *Escherichia coli*, and it was confirmed that they all show the same and high antibacterial performance. It was also confirmed that they have antifungal performance.

Tungsten oxide microparticles or tungsten oxide complex microparticles were contained in zeolite, activated carbon, and porous ceramics, and they were used for filters and building materials. It was confirmed that generation of bacteria and fungi can be decreased. Therefore, the application of the above antibacterial material makes it possible to provide films and members which exhibit practical antibacterial performance for a long period.

In addition, a paint was produced using tungsten oxide microparticles or tungsten oxide complex microparticles and coated onto the glass of a bathroom, and it was confirmed that growth of mold was decreased. When the glass onto which the paint was coated was evaluated for hydrophilicity, it was confirmed that a contact angle was one degree or less and superhydrophilicity was exhibited. Therefore, the glass became not easy to get dirty. The antibacterial materials of the examples are excellent in performance of decomposing organic gas such as acetaldehyde, the film of the antibacterial material has a high transmission rate, and a problem of visual color unevenness or the like is not caused readily. Therefore, it can also be used suitably for the members used in automotive interiors, and the building materials, interior materials, home electric appliances and the like used for factories, shops, schools, public facilities, hospitals, welfare facilities, accommodation facilities, houses and the like.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A method for using an antibacterial material, the method comprising:
   preparing the antibacterial material comprising tungsten oxide complex microparticles which contain 50 mass % or more of tungsten oxide, and at least one metal element selected from the group consisting of Ti, Zr, Mn, Fe, Pd, Pt, Cu, Ag, Ce, Zn, and Al in a range of 0.001 mass % or more and 10 mass % or less; and
   using the antibacterial material in a dark place; wherein:
   the tungsten oxide complex microparticles have an average primary particle size in a range of 1 nm or more and 200 nm or less, and a BET specific surface area in a range of 4.1 m$^2$/g or more and 820 m$^2$/g or less, and
   the tungsten oxide complex microparticles have:
   an antibacterial activity value R of 1 or more expressed by the following:

$R=\log(B_1/C_1),$ where $B_1$ denotes an average value of viable cell count after storing an untreated test piece for 24 hours, and $C_1$ denotes an average value of viable cell count after storing the test piece on which the tungsten oxide complex microparticles are coated for 24 hours, wherein the antibacterial activity value R is determined according to an antibacterial property evaluation test to evaluate viable cell count by inoculating in a test piece, to which the antibacterial microparticles are adhered in a range of 0.02 mg/cm$^2$ or more and 40 mg/cm$^2$ or less, at least one bacterium selected from among *Staphylococcus aureus*, *Escherichia coli*, *Klebsiella pneumoniae*, *Pseudomonas aeruginosa*, methicillin-resistant *Staphylococcus aureus*, and enterohemorrhagic *Escherichia coli*, and storing for 24 hours by a method according to Antimicrobial products—Test for antimicrobial activity of JIS-Z-2801 (2000);
   an antibacterial activity value Ro of 2.8 or more expressed by the following:

$R_D=\log(B_D/C_D,$ wherein $B_D$ denotes an average value of viable cell count after storing an untreated test piece in a dark place for 24 hours, and $C_D$ denotes an average value of viable cell count after storing the test piece on which the tungsten oxide complex microparticles are coated in a dark place for 24 hours;
   an antibacterial activity value $R_{L6h}$ of 2.5 or more, determined according to the following:

$R_{L6h}=\log(B_{L6h}/C_{L6h}),$ where $B_{L6h}$ denotes an average value of viable cell count after storing an untreated test piece under visible light having a wavelength of 380 nm or more and an illuminance of 6000 lx for six hours, and $C_{L6h}$ denotes an average value of viable cell count after storing the test piece on which the tungsten oxide complex microparticles are coated under the visible light having wavelength of 380 nm or more and an illuminance of 6000 lx for six hours; and an antibacterial activity value $R_{L1000}$ of 4.5 or more, determined according to the following:

$$R_{L1000}=\log(B_{L1000}/C_{L1000}),$$

where $B_{L1000}$ denotes an average value of viable cell count after storing an untreated test piece under visible light having wavelength of 380 nm or more and an illuminance of 1000 lx for 24 hours, and $C_{L1000}$ denotes an average value of viable cell count after storing the test piece on which the tungsten oxide complex microparticles are coated under the visible light having wavelength of 380 nm or more and an illuminance of 1000 lx for 24 hours;

the antibacterial material exhibits antibacterial performance in the dark place; and wherein:

the tungsten oxide which constructs the tungsten oxide complex microparticles has a crystalline structure including a mixture of: a monoclinic crystal and a triclinic crystal of tungsten trioxide; the monoclinic crystal and an orthorhombic crystal of tungsten trioxide; the triclinic crystal and the orthorhombic crystal; or the monoclinic crystal, the triclinic crystal, and the orthorhombic crystal; and the tungsten oxide complex microparticles measured by an X-ray diffraction method have a first peak, a second peak, and a third peak in a 2θ range of 22.5 degrees or more and 25 degrees or less, and an intensity ratio (A/D) of a peak A to a peak D and an intensity ratio (B/D) of a peak B to the peak D each are in a range of 0.5 to 2.0, and an intensity ratio (C/D) of a peak C to the peak D is in a range of 0.4 to 2.5, wherein the peak A is a peak having a 2θ range of 22.8 to 23.4 degrees, the peak B is a peak having a 2θ range of 23.4 to 23.8 degrees, the peak C is a peak having a 2θ range of 24.0 to 24.25 degrees, and the peak D is a peak having a 2θ range of 24.25 to 24.5 degrees, in an X-ray diffraction chart of the tungsten oxide complex microparticles.

2. The method according to claim 1, wherein the intensity ratio (A/D) of the peak A to the peak D and the intensity ratio (B/D) of the peak B to the peak D each are in a range of 0.7 to 2.0, and the intensity ratio (C/D) of the peak C to the peak D is in a range of 0.5 to 2.5.

3. The method according to claim 1, wherein the crystalline structure of the tungsten oxide comprises the monoclinic crystal, the triclinic crystal, and the orthorhombic crystal.

4. The method according to claim 1, wherein the tungsten oxide complex microparticles have an antibacterial activity value $R_L$ of 1.0 or more expressed by the following:

$$R_L=\log(B_L/C_L),$$

where $B_L$ denotes an average value of viable cell count after storing an untreated test piece under the visible light having a wavelength of 380 nm and an illuminance of 6000 lx for 24 hours, and $C_L$ denotes an average value of viable cell count after storing the test piece on which the tungsten oxide complex microparticles are coated under the visible light having wavelength of 380 nm and illuminance of 6000 lx for 24 hours, as determined by an antibacterial property evaluation test using a white fluorescent lamp and an UV cut filter.

5. The method according to claim 1, wherein the tungsten oxide complex contains at least one metal element selected from the group consisting of Cu, Ag and Zn in a range of 0.001 mass % or more and 1 mass % or less.

6. The method according to claim 1, wherein:

the tungsten oxide complex comprises at least one metal element selected from the group consisting of Ti, Zr, Mn, Fe, Pd, Pt, Cu, Ag, Ce, Zn, and Al in at least one form selected from the group consisting of a single element and a compound.

7. The method according to claim 1, wherein the antibacterial material is added to or impregnated into a base member.

8. The method according to claim 1, wherein the antibacterial material is added to or impregnated into a film to constitute an antibacterial film.

9. The method according to claim 8, wherein the antibacterial film contains an inorganic binder in a range of 5 to 95 mass %.

* * * * *